(12) United States Patent
Hosokawa et al.

(10) Patent No.: US 11,512,338 B2
(45) Date of Patent: Nov. 29, 2022

(54) **CULTURE MEDIUM FOR DETECTION OF BACTERIUM BELONGING TO GENUS *LISTERIA***

(71) Applicant: NISSUI PHARMACEUTICAL CO., LTD., Taito-ku (JP)

(72) Inventors: Shuhei Hosokawa, Yuki (JP); Shingo Mizuochi, Yuki (JP); Mitsuaki Kashida, Yuki (JP)

(73) Assignee: NISSUI PHARMACEUTICAL CO., LTD., Taito-ku (JP)

( * ) Notice: Subject to any disclaimer, the term of this patent is extended or adjusted under 35 U.S.C. 154(b) by 285 days.

(21) Appl. No.: 16/618,985

(22) PCT Filed: Jun. 7, 2018

(86) PCT No.: PCT/JP2018/021855
§ 371 (c)(1),
(2) Date: Dec. 3, 2019

(87) PCT Pub. No.: WO2018/225821
PCT Pub. Date: Dec. 13, 2018

(65) Prior Publication Data
US 2021/0079439 A1    Mar. 18, 2021

(30) Foreign Application Priority Data

Jun. 9, 2017   (JP) .............................. JP2017-114054

(51) Int. Cl.
*C12Q 1/04* (2006.01)
*C12N 1/20* (2006.01)
*C12N 5/00* (2006.01)

(52) U.S. Cl.
CPC ............... *C12Q 1/04* (2013.01); *C12N 1/20* (2013.01); *C12N 5/0068* (2013.01); *C12Y 301/04011* (2013.01); *C12Y 302/01021* (2013.01); *C12Q 2563/107* (2013.01)

(58) Field of Classification Search
CPC ............ C12Q 1/04; C12Q 2563/107; C12Q 2334/22; C12Q 2334/52; C12Q 1/10; C12Q 1/045; C12N 1/20; C12N 5/0068; C12Y 302/01021; C12Y 301/04011
See application file for complete search history.

(56) References Cited

U.S. PATENT DOCUMENTS 6,228,606 B1   5/2001   Facon et al.
6,638,755 B1   10/2003  Mizuochi et al.
2007/0259393 A1   11/2007   Restaino
2010/0279330 A1   11/2010   Asir et al.
2016/0040211 A1*  2/2016   Salter ................ C12Q 1/045
                                                       435/34

FOREIGN PATENT DOCUMENTS

| EP | 1 179 586 A1 | 2/2002 |
| EP | 2 235 202 B1 | 6/2013 |
| JP | 9-19282 A | 1/1997 |
| JP | 2000-325072 A | 11/2000 |
| JP | 2001-510054 A | 7/2001 |
| JP | 2007-61061 A | 3/2007 |
| JP | 2011-509680 A | 3/2011 |
| JP | 2012-130274 A | 7/2012 |

OTHER PUBLICATIONS

Stessl et al., Journal of Applied Microbiology, 2009, vol. 106, p. 651-659.*
Phan-Thanh et al., International Journal of Food Microbiolgy, 1997, vol. 35, p. 91-95.*
Extended European Search Report dated Jan. 29, 2021 in European Patent Application No. 18814000.8, 8 pages.
Luc Bauwens, et al., "Detection of Pathogenic *Listeria* spp. in Zoo Animal Faeces: use of Immunomagnetic Separation and a Chromogenic Isolation Medium" Veterinary Microbiology, vol. 91. Issues 2-3, XP55766808, Feb. 1, 2003, pp. 115-123.
"ALOA™ (Agar Listeria According to Ottaviani & Agosti) p. 1/2" AES Chemunex, Retreived from the Internet: URL: https://www.mibius.de/out/oxbaseshop/html/0/images/wysiwigpro/ALOA_Agar_520080S_TI.pdf, [retreived on Jan. 20, 2021] XP55767165, Jun. 30, 2008, pp. 1-2.
Jodi Woan-Fei Law, et al., "An Insight into the Isolation, Enumeration, and Molecular Detection of *Listeria* Monocytogenes in Food" Frontiers Microbiology, vol. 6, XP55766826, Nov. 3, 2015, 15 pages.
International Search Report dated Aug. 21, 2018 in PCT/JP2018/021855 filed Jun. 7, 2018, 2 pages.
"Standard methods of analysis in food safety regulation, microorganism," Japan Food Hygiene Association, 2015, pp. 340-363, 13 pages total.

* cited by examiner

*Primary Examiner* — Kade Ariani
(74) *Attorney, Agent, or Firm* — Oblon, McClelland, Maier & Neustadt, L.L.P.

(57) ABSTRACT

A medium containing (A) a chromogenic substance which develops a color when decomposed by β-glucosidase or a fluorogenic substance which develops a fluorescence when decomposed by β-glucosidase; (B) a chromogenic substance which develops a color when decomposed by phosphatidyl inositol-specific phospholipase C or a fluorogenic substance which develops a fluorescence when decomposed by phosphatidyl inositol-specific phospholipase C; and (C) a sugar that is useful for the detection of *Listeria monocytogenes* and/or *Listeria ivanovii*.

6 Claims, No Drawings

CULTURE MEDIUM FOR DETECTION OF BACTERIUM BELONGING TO GENUS *LISTERIA*

FIELD OF THE INVENTION

The present invention relates to a medium for detecting *Listeria monocytogenes* and *Listeria ivanovii* in a simple and specific manner, and a detection method thereof.

BACKGROUND OF THE INVENTION

A bacterium belonging to the genus *Listeria* is a gram-positive, facultatively anaerobic, and asporogenic short bacillus. Currently, *Listeria* (hereinafter referred to simply as "*L.*") *monocytogenes, L. ivanovii, L. innocua, L. welshimeri, L. seeligeri, L. grayi, L. marthii, L. rocourtiae, L. fleischmannii, L. weihenstephanensis, L. aquatica, L. cornellensis, L. floridensis, L. grandensis, L. riparia*, and the like exist. Among these, the only one that is usually pathogenic to a human is *L. monocytogenes*, and thus this bacterium becomes a target for food inspection. But a food product is often contaminated with several types of *Listeria* bacteria other than *L. monocytogenes*, for example *L. innocua*, and therefore it is important to differentiate *L. monocytogenes* from these bacteria (Non Patent Literature 1). *L. monocytogenes* is also known to cause a zoonosis, and is a bacterium which also becomes a target for environmental inspection in the United States.

Standard test methods for the genus *Listeria* performed in Japan include a qualitative test and a quantitative test. In the qualitative test, a specimen is subjected to a primary enrichment culture in a half-Fraser broth and further subjected to a secondary bacterial enrichment culture using a Fraser broth, and then, a selective isolation medium which comprises an enzyme substrate (an enzyme substrate culture medium) is used to isolate the *Listeria* bacteria. In this test, a method of seeding a colony obtained from the primary bacterial enrichment culture on the enzyme substrate culture medium without the secondary bacterial enrichment culture is performed in parallel. On the other hand, in the quantitative test, after a specimen is cultured for resuscitation in a BPW culture medium (20±2° C., 1 hour±5 minutes), the enzyme substrate culture medium is used to isolate the *Listeria* bacteria. Examples of known methods for identifying *L. monocytogenes* after culture using the enzyme substrate culture medium in the qualitative test and the quantitative test include a carbohydrate degradation test and a CAMP test, but these tests require culturing and thus take time for identification. Therefore, for example, a rapid determination method using a PCR technique or an immunodiagnostic technique is known as a supplementary method for identifying *L. monocytogenes* (Non Patent Literature 1). For example, a detection method based on a LAMP technique, which is a kind of PCR technique, is known as means for differentiating a bacterial species belonging to the genus *Listeria* (Patent Literature 1). However, this LAMP technique is a method which uses four types of bacterial species-specific primers, and thus is not means which can be used in an ordinary laboratory.

The means which uses the selective isolation medium as described above is convenient as the means for differentiating the bacterial species belonging to the genus *Listeria*. Examples of such a selective isolation medium include an ALOA® agar culture medium (available from Sysmex bioMerieux Co., Ltd.) using a chromogenic substance, which develops a color when decomposed by β-glucosidase, and CHROMagar® *Listeria* (available from CHROMagar), which are known. The above described enzyme substrate culture medium exhibits a typical blue-green colony with a milky-white halo when *L. monocytogenes* was seeded thereon, but exhibits no halo when *Listeria* bacteria other than *L. monocytogenes* were seeded thereon. Another known example of the medium using a chromogenic substance, which develops a color when decomposed by β-glucosidase, is the medium of Patent Literature 2. A medium comprising a chromogenic substrate which is specifically cleaved by phosphatidyl inositol-specific phospholipase C (PIPL C) (Patent Literature 3) is also known.

CITATION LIST

Patent Literature

Patent Literature 1: JP-A-2007-61061
Patent Literature 2: JP-A-2012-130274
Patent Literature 3: JP-A-2001-510054

Non Patent Literature

Non Patent Literature 1: Japan Food Hygiene Association (2015). Standard methods of analysis in food safety regulation, microorganism, 2015, pp. 340-363

SUMMARY OF THE INVENTION

Problems to be Solved by the Invention

However, it is difficult to clearly differentiate between *L. monocytogenes* and *L. ivanovii* among the *Listeria* bacteria by using the above described enzyme substrate culture medium and the selective isolation media of Patent Literatures 2 and 3. Accordingly, a confirmatory test needs to be carried out by using the colony obtained from the enzyme substrate culture medium, which takes time and effort and is troublesome.

Therefore, it is an object of the present invention to provide means for detecting *L. monocytogenes* and/or *L. ivanovii*, which is pathogenic to a human and causes food contamination, in a convenient and specific manner.

Means for Solving the Problems

The present inventor has carried out various studies to solve the above described problem and has found the following fact and accomplished the present invention: using a sugar in combination with a chromogenic substance or a fluorogenic substance which develops a color when decomposed by β-glucosidase and a chromogenic substance or a fluorogenic substance which develops a color when decomposed by phosphatidyl inositol-specific phospholipase C (PIPL C) enables clear differentiation between *L. ivanovii* and *L. monocytogenes*, in terms of the color or fluorescence of a colony but not a change in the color surrounding the colony.

Specifically, the present invention provides the following inventions [1] to [7]:
[1] A culture medium for detection of *L. monocytogenes* and/or *L. ivanovii*, comprising the following components (A), (B), and (C):
(A) a chromogenic substance which develops a color when decomposed by β-glucosidase, or a fluorogenic substance which develops a fluorescence when decomposed by β-glucosidase;

(B) a chromogenic substance which develops a color when decomposed by phosphatidyl inositol-specific phospholipase C, or a fluorogenic substance which develops a fluorescence when decomposed by phosphatidyl inositol-specific phospholipase C; and (C) a sugar.

[2] The culture medium for detection of *L. monocytogenes* and/or *L. ivanovii* according to [1], wherein the sugar as component (C) is glucose.

[3] The culture medium for detection of *L. monocytogenes* and/or *L. ivanovii* according to [1] or [2], wherein the culture medium comprises the sugar as component (C) at a concentration at the time of detection of 2 g/L or more and 30 g/L or less.

[4] The culture medium for detection of *L. monocytogenes* and/or *L. ivanovii* according to any of [1] to [3], wherein component (A) is 5-bromo-4-chloro-3-indoxyl-β-D-glucopyranoside. [5] The culture medium for detection of *L. monocytogenes* and/or *L. ivanovii* according to any of [1] to [3], wherein component (A) is 4-methyl umbelliferyl-β-D-glucopyranoside.

[6] The culture medium for detection of *L. monocytogenes* and/or *L. ivanovii* according to any of [1] to [5], wherein a composition additionally comprising (D) a gelling agent and (E) a nutritional component for a bacterial cell other than component (C) is supported or layered on a fibrous water-absorbing sheet.

[7] A method for detecting *L. monocytogenes* and/or *L. ivanovii*, comprising the steps of seeding and culturing a specimen on the culture medium according to any of [1] to [6] and then detecting the color or fluorescence of a colony which appeared on the culture medium.

Advantageous Effects of Invention

Using the culture medium of the present invention allows for selectively detecting a bacterium belonging to the genus *Listeria* and clearly differentiating, among bacterial species belonging to the genus *Listeria*, *L. monocytogenes* and/or *L. ivanovi* from other bacterial species of the genus *Listeria* based on the color or fluorescence of the colony. Furthermore, the need to conduct a confirmatory test for *L. monocytogenes* and/or *L. Ivanovii* is eliminated, and thus, time and effort for an inspection can be reduced.

DETAILED DESCRIPTION OF THE INVENTION

The culture medium for detection of *L. monocytogenes* and/or *L. ivanovii* of the present invention comprises the following components (A), (B), and (C):

(A) a chromogenic substance which develops a color when decomposed by β-glucosidase, or a fluorogenic substance which develops a fluorescence when decomposed by β-glucosidase;

(B) a chromogenic substance which develops a color when decomposed by phosphatidyl inositol-specific phospholipase C, or a fluorogenic substance which develops a fluorescence when decomposed by phosphatidyl inositol-specific phospholipase C; and (C) a sugar.

Component (A) is for detecting a colony of *Listeria* bacteria, wherein the action of β-glucosidase from the *Listeria* bacteria leads to release of a detectable releasable group, resulting in color development. Examples of such a releasable group include a chromogenic compound and a fluorogenic compound. Specific examples of a substrate for β-glucosidase include 5-bromo-4-chloro-3-indoxyl-β-D-glucopyranoside (X-β-glucoside, blue), 5-bromo-6-chloro-3-indoxyl-β-D-glucopyranoside (MAGENTA-β-glucopyranoside, reddish violet), 5-bromo-6-chloro-3-indolyl-β-D-glucopyranoside (reddish violet), 6-chloro-3-indolyl-β-D-glucopyranoside (pink), 5-bromo-3-indolyl-s-D-glucopyranoside, 4-methyl umbelliferyl-β-D-glucopyranoside, o-nitrophenyl-β-D-glucopyranoside, phenyl-β-D-glucopyranoside, 3-nitrophenyl-β-D-glucopyranoside, 4-nitrophenyl-β-D-glucopyranoside, 3-indoxyl-β-glucopyranoside trihydrate, n-heptyl-f-D-glucopyranoside, and 5-bromo-4-chloro-3-indoxyl-2-acetamido-2-deoxy-β-D-glucopyranoside. Among these, 5-bromo-4-chloro-3-indoxyl-β-D-glucopyranoside (X-β-glucoside) and 4-methyl umbelliferyl-β-D-glcopyranoside are preferred in terms of detectability of *L. monocytogenes*. The concentration of the β-glucosidase substrate having the detectable releasable group is, as a concentration at the time of detection, preferably 0.001 g/L or more and 5 g/L or less, especially preferably 0.01 g/L or more and 0.25 g/L or less, and more preferably 0.02 g/L or more and 0.15 g/L or less.

Component (B) is for detecting a colony of *L. monocytogenes* and/or *L. ivanovii*, wherein the action of PIPL C from the *Listeria* bacteria leads to release of a detectable releasable group, resulting in color development. Examples of such a releasable group include a chromogenic compound and a fluorogenic compound. Examples of such a substrate for PIPL C include a compound described in JP-B-5711218, and inositol phosphate which has a chromophore such as a 5-bromo-4-chloro-3-indoxyl group, a 5-bromo-6-chloro-3-indoxyl group, and a 6-chloro-3-indoxyl group is preferred. These compounds are preferably used in the form of a salt such as a sodium salt, a potassium salt, and an ammonium salt. Examples of a preferable commercial product include Aldol 514® inositol-phosphate, ammonium salt (available from Biosynth) and Aldol 495® inositol-phosphate, ammonium salt (available from Biosynth). The concentration of compound (B) is, as a concentration at the time of detection, preferably 0.001 g/L or more and 5 g/L or less, more preferably 0.05 g/L or more and 2 g/L or less, and even more preferably 0.1 g/L or more and 1 g/L or less.

Component (C), the sugar, is not particularly limited as long as the *Listeria* bacteria can use the sugar. For example, glucose, fructose, galactose, mannose, mannite, sorbitol, dulcite, inositol, arabinose, xylose, rhamnose, and adonite are preferable, and glucose is more preferable in terms of the glucose metabolism ability of *L. monocytogenes* and *L. ivanovii*. Component (C) has the effect of making the color or fluorescence of the colony of *L. monocytogenes* and *L. ivanovii* clear and making detection of *L. monocytogenes* and *L. ivanovii* easy and accurate. The content of component (C) is, as a concentration at the time of detection, preferably 2 g/L or more and 30 g/L or less in terms of the ability to make the colony color clear and in terms of the growth of the *Listeria* bacteria. The concentration of component (C) is more preferably 5 g/L or more and 30 g/L or less, and even more preferably 5 g/L or more and 20 g/L or less in terms of the ability to make the colony color clear.

For further enhancing the selectivity for the *Listeria* bacteria, the culture medium of the present invention preferably comprises one or more selected from the group consisting of moxalactam and colistin sulfate, and more preferably comprises moxalactam and colistin sulfate. The content of moxalactam is, as a concentration at the time of detection, preferably 0.001 g/L or more and 0.5 g/L or less, more preferably 0.005 g/L or more and 0.3 g/L or less, and even more preferably 0.01 g/L or more and 0.2 g/L or less, in terms of the selectivity for the *Listeria* bacteria. The content of the colistin sulfate is preferably 0.001 g/L or more and 0.5 g/L or less, more preferably 0.005 g/L or more and 0.2 g/L or less, and even more preferably 0.005 g/L or more and 0.1 g/L or less.

In addition to the components described above, the culture medium of the present invention may comprise a nutritional component for a bacterial cell other than component (C), an inorganic salt, a saccharide, and/or a pH adjustor. Examples of the nutritional component for a bacterial cell include peptone, yeast extract, meat extract, and fish extract.

Examples of the inorganic salt include a metal salt of an inorganic acid such as sodium chloride and sodium thiosulfate; and a metal salt of an organic acid such as ferric ammonium citrate and sodium citrate. Furthermore, examples of other inorganic salts include bile powder, sodium cholate, and sodium deoxycholate. A monosaccharide and an oligosaccharide can be used as a saccharide. Examples thereof include lactose, sucrose (white soft sugar), xylose, cellobiose, and maltose.

The form of the culture medium of the present invention is not particularly limited. In addition to an ordinary agar culture medium, the culture medium of the present invention may be in the form of a sheet-shaped simple culture medium (JP-A-57-502200 and JP-A-6-181741) or may have a structure in which the culture medium is supported on, for example, a fibriform water-absorbing sheet having a mesh (JP-A-9-19282 and JP-A-2000-325072). Among these, a preferable simple culture medium is the one in which a composition is supported or layered on a fibrous water-absorbing sheet, the composition comprising, in addition to the above components (A) to (C), and as necessary moxalactam and colistin sulfate, (D) a gelling agent and (E) a nutritional component for a bacterial cell other than component (C).

In this context, examples of the gelling agent include a water-soluble gelling agent, that is, a macromolecule which readily disperses in water and gelates. Specific examples thereof include pectin, guar gum, xanthan gum, tamarind gum, locust bean gum, gellan gum, gum arabic, tara gum, carrageenan, and carboxymethylcellulose. Among these, pectin, guar gum, and xanthan gum are more preferable and xanthan gum is especially preferable in terms of dispersibility in water, stability of the gel, and the like.

The fibrous water-absorbing sheet used in the present invention needs to be a sheet in which a liquid specimen seeded thereon diffuses readily by a capillary phenomenon and examples thereof include a nonwoven fabric made from synthetic fibers, typically such as a rayon nonwoven fabric and a nonwoven fabric made from natural fibers, typically such as a cotton nonwoven fabric. The shape of these sheets is not particularly limited and may be any of a square, a rectangle, a circle, and other shapes. Although the size of these sheets is not particularly limited either, the sheet preferably has a longest diameter of 1 cm or more and 15 cm or less in view of the fact that the sheet is used for simple detection. Furthermore, the sheet preferably has a mesh size of 15 mesh or more and 100 mesh or less, and particularly 20 mesh or more and 50 mesh or less and has a thickness of 10 μm or more and 1,000 μm or less, and particularly 50 μm or more and 600 μm or less.

Such a fibrous water-absorbing sheet is preferably placed on a waterproof flat plate. Although such a waterproof flat plate may be made of any material such as plastic and glass as long as the material is waterproof, the plate is preferably transparent for observation from the outside.

Examples of specimens to be measured using the culture medium of the present invention include a dairy product, a meat product, a salad, a ready-to-eat food product, an environmental specimen (water, soil, and the like), and a clinical specimen (a human, a cow, a sheep, a pig, a goat, and the like). A culture solution obtained by preculturing these specimens in a Trypto-Soya broth culture medium and a culture solution obtained by culturing these specimens in a culture medium for enrichment can also be used as a sample.

Detection of *L. monocytogenes* and/or *L. ivanovii* by using the culture medium of the present invention is performed by seeding and culturing the specimen on the culture medium and observing the property thereof such as color development and fluorescence of a colony. Usually, this culturing is preferably performed at 25 to 35° C. for 24 to 72 hours.

For detection of *L. monocytogenes* and/or *L. ivanovii* by using the simple culture medium of the present invention, the liquid specimen is seeded on the surface of the culture medium. Then, the liquid specimen diffuses readily by the capillary phenomenon through the three-dimensional cavities of the meshes, and subsequently swells and gelates. Consequently, *L. monocytogenes* and *L. ivanovii* in the liquid specimen are entrapped, inhibited from free migration, and cultured to form a colony. Therefore, the formed colony can be found readily by observing the surface which defines the culture medium. A bacterial count can be calculated readily by seeding a sample on the simple culture medium quantitatively and counting colonies which appeared after culture.

A method of seeding an aliquot with for example a pipette is usually used for seeding liquid which comprises bacterial cells, but a stamp method, that is, a method of pressing the culture medium against an specimen with a high water content and a method of immersing the culture medium in a liquid specimen may also be used. Culture after seeding of the liquid specimen may be performed in a stationary manner or may be performed during transportation.

EXAMPLES

Hereinbelow, the present invention will be described in detail by way of examples, but the present invention is not limited by these examples at all.

Example 1 (Agar Culture Medium Comprising Color-Developing Substrate)

A culture medium formulation is shown in Table 1. Components of this culture medium formulation were added to 1 liter of purified water, autoclaved at 121° C. for 15 minutes, and cooled to about 50° C. Then, 20 mL aliquots were dispensed aseptically in plastic petri dishes (90 mm in diameter) and allowed to stand until the culture medium set, thereby producing the culture medium of the present invention.

Culture media which comprised glucose in an amount of 0, 2, 5, 20, or 30 g/L instead of the amount shown in Table 1 were also produced.

TABLE 1

| Composition | g/L |
| --- | --- |
| Meat peptone | 18.00 g |
| Casein peptone | 6.00 g |
| Yeast extract | 10.00 g |

TABLE 1-continued

| Composition | g/L |
|---|---|
| Magnesium sulfate (anhydrous) | 0.50 g |
| Magnesium glycerophosphate | 1.0 g |
| Sodium chloride | 5.0 g |
| Lithium chloride | 10.0 g |
| Disodium hydrogenphosphate | 2.50 g |
| Colistin sulfate | 0.01 g |
| Moxalactam | 0.02 g |
| Agar | 15.00 g |
| Silicon dioxide | 10.00 g |
| Aldol514 ™ inositol-phosphate, ammonium salt(Biosynth) | 0.30 g |
| 5-Brom-4-Chloro-3-indoxyl-beta-D-glucopyranoside(Biosynth) | 0.05 g |
| Glucose | 10.00 g |

A strain to be tested was precultured in a sheep blood agar culture medium for 24 hours and the resulting colony was suspended in sterile saline to prepare a bacterial suspension. Each bacterial suspension was used for inoculation by streaking with a platinum loop. Color developed by the colony after culture at 37° C. for 44 hours is shown in Table 2.

TABLE 3

| Composition | g/L |
|---|---|
| Meat peptone | 18.00 g |
| Casein peptone | 6.00 g |
| Yeast extract | 10.00 g |
| Magnesium sulfate (anhydrous) | 0.50 g |
| Magnesium glycerophosphate | 1.0 g |
| Sodium chloride | 5.0 g |
| Lithium chloride | 10.0 g |
| Disodium hydrogenphosphate | 2.50 g |
| Colistin sulfate | 0.01 g |
| Moxalactam | 0.02 g |
| Agar | 15.00 g |
| Silicon dioxide | 10.00 g |
| Aldol514 ™ inositol-phosphate, ammonium salt(Biosynth) | 0.30 g |
| 4-Methylumbelliferyl-beta-D-glucopyranoside(Biosynth) | 0.1 g |
| Glucose | 10.00 g |

A strain to be tested was precultured in a sheep blood agar culture medium for 24 hours and the resulting colony was suspended in sterile saline to prepare a bacterial suspension. Each bacterial suspension was used for inoculation by

TABLE 2

| Strain | 0 g/L | 2 g/L | 5 g/L | 10 g/L | 20 g/L | 30 g/L |
|---|---|---|---|---|---|---|
| Listeria monocytogenes ATCC15313 | Red Surrounding area: Blue | Red Surrounding area: Blue | Red Surrounding area: Blue | Red Surrounding area: Blue | Red Surrounding area: Blue | Red Surrounding area: Blue |
| Listeria monocytogenes NS5168 | Red Surrounding area: Blue | Red Surrounding area: Blue | Red Surrounding area: Blue | Red Surrounding area: Blue | Red Surrounding area: Blue | Red Surrounding area: Blue |
| Listeria monocytogenes NS5169 | Red Surrounding area: Blue | Red Surrounding area: Blue | Red Surrounding area: Blue | Red Surrounding area: Blue | Red Surrounding area: Blue | Red Surrounding area: Blue |
| Listeria monocytogenes NS5170 | Red Surrounding area: Blue | Red Surrounding area: Blue | Red Surrounding area: Blue | Red Surrounding area: Blue | Red Surrounding area: Blue | Red Surrounding area: Blue |
| Listeria ivanovii JCM7681 | Red Surrounding area: Blue | Red Surrounding area: Pale blue | Red | Red | Red | Red |
| Listeria ivanovii NS5167 | Red Surrounding area: Blue | Red Surrounding area: Pale blue | Red | Red | Red | Red |
| Listeria innocua NS5166 | Blue | Blue | Blue | Blue | Blue | Blue |
| Listeria welshimeri NS5172 | Blue | Blue | Blue | Blue | Blue | Blue |

Table 2 indicates that using the agar culture medium which comprised 2 g/L to 30 g/L glucose as component (C) in addition to component (A) and component (B) allowed for clearly differentiating the colonies of *L. monocytogenes* and *L. ivanovii* from the colonies of other *Listeria* bacteria.

Example 2 (Agar Culture Medium Comprising Fluorogenic Substrate)

A culture medium formulation is shown in Table 3. Components of this culture medium formulation were added to 1 liter of purified water, autoclaved at 121° C. for 15 minutes, and cooled to about 50° C. Then, 20 mL aliquots were dispensed aseptically in plastic petri dishes (90 mm in diameter) and allowed to stand until the culture medium set, thereby producing the culture medium of the present invention.

streaking with a platinum loop. Color developed by the colony and the presence or absence of fluorescence after culture at 37° C. for 44 hours are shown in Table 4.

TABLE 4

| Strain | Color developed by colony | Presence or absence of fluorescence |
|---|---|---|
| Listeria monocytogenes ATCC15313 | Red | + |
| Listeria monocytogenes NS5168 | Red | + |
| Listeria monocytogenes NS5169 | Red | + |
| Listeria monocytogenes NS5170 | Red | + |
| Listeria ivanovii JCM7681 | Red | − |
| Listeria ivanovii NS5167 | Red | − |
| Listeria innocua NS5166 | White | + |
| Listeria welshimeri NS5172 | White | + |

Table 4 indicates that using the agar culture medium which comprised 10 g/L glucose as component (C) in addition to component (A) and component (B) allowed for clearly differentiating the colonies of *L. monocytogenes* and *L. ivanovii* from the colonies of other *Listeria* bacteria.

Example 3 (Simple Culture Medium Comprising Color-Developing Substrate)

A culture medium formulation is shown in Table 5. Components of this culture medium formulation were added to 1,000 mL of ethanol solution to prepare a suspension thereof. 1 mL aliquots of this suspension in ethanol were dispensed aseptically in containers (50 mm in diameter) holding a fibrous water-absorbing sheet (a cotton nonwoven fabric, 50 mm in diameter), and then were allowed to stand overnight to dry in a closed space in such a manner that the containers did not overlap. Then, a lid was put on the container, thereby producing the simple culture medium of the present invention.

TABLE 5

| Composition | g/L |
|---|---|
| Meat peptone | 18.00 g |
| Casein peptone | 6.00 g |
| Yeast extract | 10.00 g |
| Magnesium sulfate (anhydrous) | 0.50 g |
| Magnesium glycerophosphate | 7.5 g |
| Sodium chloride | 5.0 g |
| Lithium chloride | 10.0 g |
| Disodium hydrogenphosphate | 2.50 g |
| Colistin sulfate | 0.01 g |
| Moxalactam | 0.02 g |
| Xanthan gum | 20.00 g |
| Silicon dioxide | 10.00 g |
| Aldol514 ™ inositol-phosphate, ammonium salt(Biosynth) | 0.30 g |
| 5-Brom-4-Chloro-3-indoxyl-beta-D-glucopyranoside(Biosynth) | 0.05 g |
| Glucose | 10.00 g |

A strain to be tested was precultured in a sheep blood agar culture medium for 24 hours and the resulting colony was suspended in sterile saline and diluted as appropriate to prepare a bacterial suspension. 1 mL aliquots of each bacterial suspension were seeded on the produced simple culture medium. Color developed by the colony after culture at 37° C. for 44 hours is shown in Table 6.

TABLE 6

| Strain | Color developed by colony |
|---|---|
| *Listeria monocytogenes* ATCC15313 | Red (Surrounding area: Blue) |
| *Listeria monocytogenes* NS5168 | Red (Surrounding area: Blue) |
| *Listeria monocytogenes* NS5169 | Red (Surrounding area: Blue) |
| *Listeria monocytogenes* NS5170 | Red (Surrounding area: Blue) |
| *Listeria ivanovii* JCM7681 | Red |
| *Listeria ivanovii* NS5167 | Red |
| *Listeria innocua* NS5166 | Blue |
| *Listeria welshimeri* NS5172 | Blue |

Table 6 indicates that using the simple culture medium which comprised 10 g/L glucose as component (C) in addition to component (A) and component (B) allowed for clearly differentiating the colonies of *L. monocytogenes* and *L. ivanovii* from the colonies of other *Listeria* bacteria.

The invention claimed is:

1. A medium suitable to detect and differentiate *Listeria monocytogenes* and/or *Listeria ivanovii* from other bacteria of the genus *Listeria*, comprising:
    a first chromogenic substance which develops a color when decomposed by β-glucosidase, or a first fluorogenic substance which develops a fluorescence when decomposed by β-glucosidase;
    a second chromogenic substance which develops a color when decomposed by phosphatidyl inositol-specific phospholipase C, or a second fluorogenic substance which develops a fluorescence when decomposed by phosphatidyl inositol-specific phospholipase C; and
    a sugar at a concentration of 5 g/L to 30 g/L at the time of detecting and differentiating *Listeria monocytogenes* and/or *Listeria ivanovii* from other bacteria of the genus *Listeria*.

2. The medium according to claim 1, wherein the sugar is glucose.

3. The medium according to claim 1, wherein the first chromogenic substance or the first fluorogenic substance is 5-bromo-4-chloro-3-indoxyl-β-D-glucopyranoside.

4. The medium according to claim 1, wherein the first chromogenic substance or the first fluorogenic substance is 4-methylumbelliferyl-β-D-glucopyranoside.

5. The medium according to claim 1, further comprising a gelling agent and a nutritional component for a bacterial cell other than the sugar, wherein said medium is supported or layered on a fibrous water-absorbing sheet.

6. A method for detecting and differentiating *Listeria monocytogenes* and/or *Listeria ivanovi* from other bacteria of the genus *Listeria*, the method comprising:
    seeding and culturing a specimen on the medium according to claim 1 and
    detecting a color or fluorescence of a colony which appeared on the medium thereby differentiating *Listeria monocytogenes* and/or *Listeria ivanovi* from other bacteria of the genus *Listeria*.

* * * * *